(12) United States Patent
Cragg et al.

(10) Patent No.: US 7,621,936 B2
(45) Date of Patent: Nov. 24, 2009

(54) SHEATH-MOUNTED ARTERIAL PLUG DELIVERY DEVICE

(75) Inventors: Andrew H. Cragg, Edina, MN (US); Mark Ashby, Laguna Nigel, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 560 days.

(21) Appl. No.: 10/754,824

(22) Filed: Jan. 9, 2004

(65) Prior Publication Data

US 2004/0158287 A1 Aug. 12, 2004

Related U.S. Application Data

(63) Continuation of application No. 09/904,445, filed on Jul. 11, 2001, now abandoned.

(60) Provisional application No. 60/218,431, filed on Jul. 14, 2000.

(51) Int. Cl.
*A61B 17/03* (2006.01)

(52) U.S. Cl. .......................... 606/213; 604/15; 128/887

(58) Field of Classification Search ................. 606/108, 606/151, 213–216; 604/58–63, 506, 15–18; 128/887, 897, 102.1
See application file for complete search history.

(56) References Cited

U.S. PATENT DOCUMENTS

| 581,235 | A | 4/1897 | Kenyon |
|---|---|---|---|
| 1,578,517 | A | 3/1926 | Hein |
| 2,086,580 | A | 7/1937 | Shirley |
| 2,465,357 | A | 3/1949 | Correll |
| 2,492,458 | A | 12/1949 | Bering, Jr. |
| 2,507,244 | A | 5/1950 | Correll |
| 2,558,395 | A | 6/1951 | Studer |
| 2,597,011 | A | 5/1952 | MacMasters |
| 2,680,442 | A | 6/1954 | Linzmayer |
| 2,761,446 | A | 9/1956 | Reed |
| 2,814,294 | A | 11/1957 | Figge |
| 2,824,092 | A | 2/1958 | Thompson |
| 2,899,362 | A | 8/1959 | Sieger, Jr. et al. |
| 3,157,524 | A | 11/1964 | Artandi |
| 3,724,465 | A | 4/1973 | Duchane |
| 4,000,741 | A | 1/1977 | Binard et al. |
| 4,323,072 | A | 4/1982 | Rosenbluth et al. |
| 4,340,066 | A | 7/1982 | Shah |
| 4,390,018 | A | 6/1983 | Zukowski |
| 4,405,314 | A | 9/1983 | Cope |
| 4,515,637 | A | 5/1985 | Cioca |
| 4,587,969 | A | 5/1986 | Gillis |
| 4,588,395 | A | 5/1986 | Lemelson |
| 4,619,261 | A | 10/1986 | Guerriero |
| 4,619,913 | A | 10/1986 | Luck et al. |
| 4,645,488 | A | 2/1987 | Matukas |
| 4,744,364 | A | 5/1988 | Kensey |

(Continued)

Primary Examiner—Anhtuan T Nguyen
Assistant Examiner—Kathleen Sonnett
(74) Attorney, Agent, or Firm—Crompton, Seager & Tufte LLC

(57) ABSTRACT

A method of facilitating hemostasis of a blood vessel puncture. The method includes the steps of inserting a tubular device into a puncture in a blood vessel to establish access to the blood vessel, providing a vessel closure system around the tubular device, introducing a hemostatic material into a space between the tubular device and vessel closure system, and delivering the hemostatic material adjacent to the puncture to facilitate hemostasis of the puncture.

17 Claims, 11 Drawing Sheets

U.S. PATENT DOCUMENTS

| | | | |
|---|---|---|---|
| 4,790,819 A | 12/1988 | Li et al. | |
| 4,829,994 A | 5/1989 | Kurth | |
| 4,850,960 A | 7/1989 | Grayzel | |
| 4,852,568 A | 8/1989 | Kensey | |
| 4,890,612 A | 1/1990 | Kensey | |
| 4,900,303 A | 2/1990 | Lemelson | |
| 4,929,246 A | 5/1990 | Sinofsky | |
| 4,936,835 A | 6/1990 | Haaga | |
| 4,950,234 A | 8/1990 | Fujioka et al. | |
| 5,007,895 A | 4/1991 | Burnett | |
| 5,021,059 A | 6/1991 | Kensey et al. | |
| 5,053,046 A | 10/1991 | Janese | |
| 5,061,274 A | 10/1991 | Kensey | |
| 5,080,655 A | 1/1992 | Haaga | |
| 5,108,421 A | 4/1992 | Fowler | |
| 5,163,904 A | 11/1992 | Lampropoulos et al. | |
| 5,167,624 A | 12/1992 | Butler et al. | |
| 5,192,300 A | 3/1993 | Fowler | |
| 5,192,301 A | 3/1993 | Kamiya et al. | |
| 5,195,988 A | 3/1993 | Haaga | |
| 5,206,028 A * | 4/1993 | Li | 424/484 |
| 5,220,926 A | 6/1993 | Jones | |
| 5,221,259 A | 6/1993 | Weldon et al. | |
| 5,275,616 A | 1/1994 | Fowler | |
| 5,290,310 A * | 3/1994 | Makower et al. | 606/213 |
| 5,310,407 A | 5/1994 | Casale | |
| 5,325,857 A | 7/1994 | Nabai et al. | |
| 5,334,216 A | 8/1994 | Vidal et al. | |
| 5,366,480 A | 11/1994 | Corriveau et al. | |
| 5,383,896 A | 1/1995 | Gershony et al. | |
| 5,383,899 A | 1/1995 | Hammerslag | |
| 5,388,588 A | 2/1995 | Nabai et al. | |
| 5,391,183 A | 2/1995 | Janzen et al. | |
| 5,419,765 A | 5/1995 | Weldon et al. | |
| 5,431,639 A | 7/1995 | Shaw | |
| 5,437,631 A * | 8/1995 | Janzen | 604/506 |
| 5,467,780 A | 11/1995 | Nabai et al. | |
| 5,478,352 A | 12/1995 | Fowler | |
| 5,479,936 A | 1/1996 | Nabai et al. | |
| 5,486,195 A | 1/1996 | Myers et al. | |
| 5,522,850 A | 6/1996 | Yomtov et al. | |
| 5,526,822 A | 6/1996 | Burbank et al. | |
| 5,529,577 A | 6/1996 | Hammerslag | |
| 5,540,715 A | 7/1996 | Katsaros et al. | |
| 5,542,914 A | 8/1996 | Van Iten | |
| 5,545,178 A * | 8/1996 | Kensey et al. | 606/213 |
| 5,558,853 A | 9/1996 | Quay | |
| 5,591,204 A * | 1/1997 | Janzen et al. | 606/213 |
| 5,591,205 A | 1/1997 | Fowler | |
| 5,601,602 A | 2/1997 | Fowler | |
| 5,645,566 A | 7/1997 | Brenneman et al. | |
| 5,649,547 A | 7/1997 | Ritchart et al. | |
| 5,653,730 A | 8/1997 | Hammerslag | |
| 5,665,107 A | 9/1997 | Hammerslag | |
| 5,676,689 A * | 10/1997 | Kensey et al. | 606/213 |
| 5,681,279 A | 10/1997 | Roper et al. | |
| 5,716,375 A | 2/1998 | Fowler | |
| 5,716,394 A * | 2/1998 | Bruchman et al. | 623/1.44 |
| 5,725,498 A | 3/1998 | Janzen et al. | |
| 5,741,223 A | 4/1998 | Janzen et al. | |
| 5,769,086 A | 6/1998 | Ritchart et al. | |
| 5,775,333 A | 7/1998 | Burbank et al. | |
| 5,810,806 A | 9/1998 | Ritchart et al. | |
| 5,830,130 A | 11/1998 | Janzen et al. | |
| 5,902,310 A | 5/1999 | Foerster et al. | |
| 5,928,266 A * | 7/1999 | Kontos | 606/213 |
| 6,007,563 A | 12/1999 | Nash et al. | |
| 6,033,427 A * | 3/2000 | Lee | 606/213 |
| 6,071,301 A | 6/2000 | Cragg et al. | |
| 6,162,192 A | 12/2000 | Cragg et al. | |

* cited by examiner

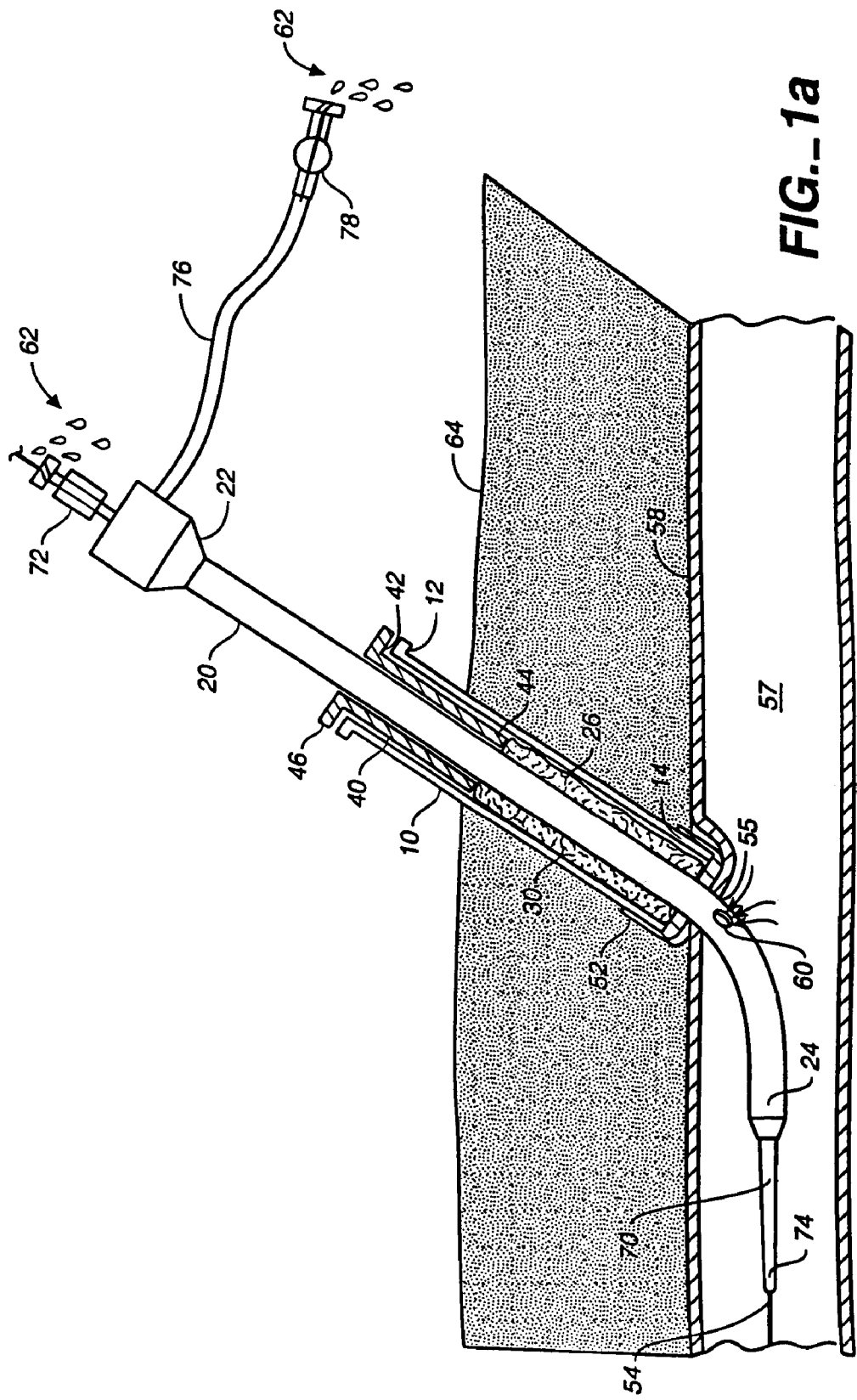
FIG._1a

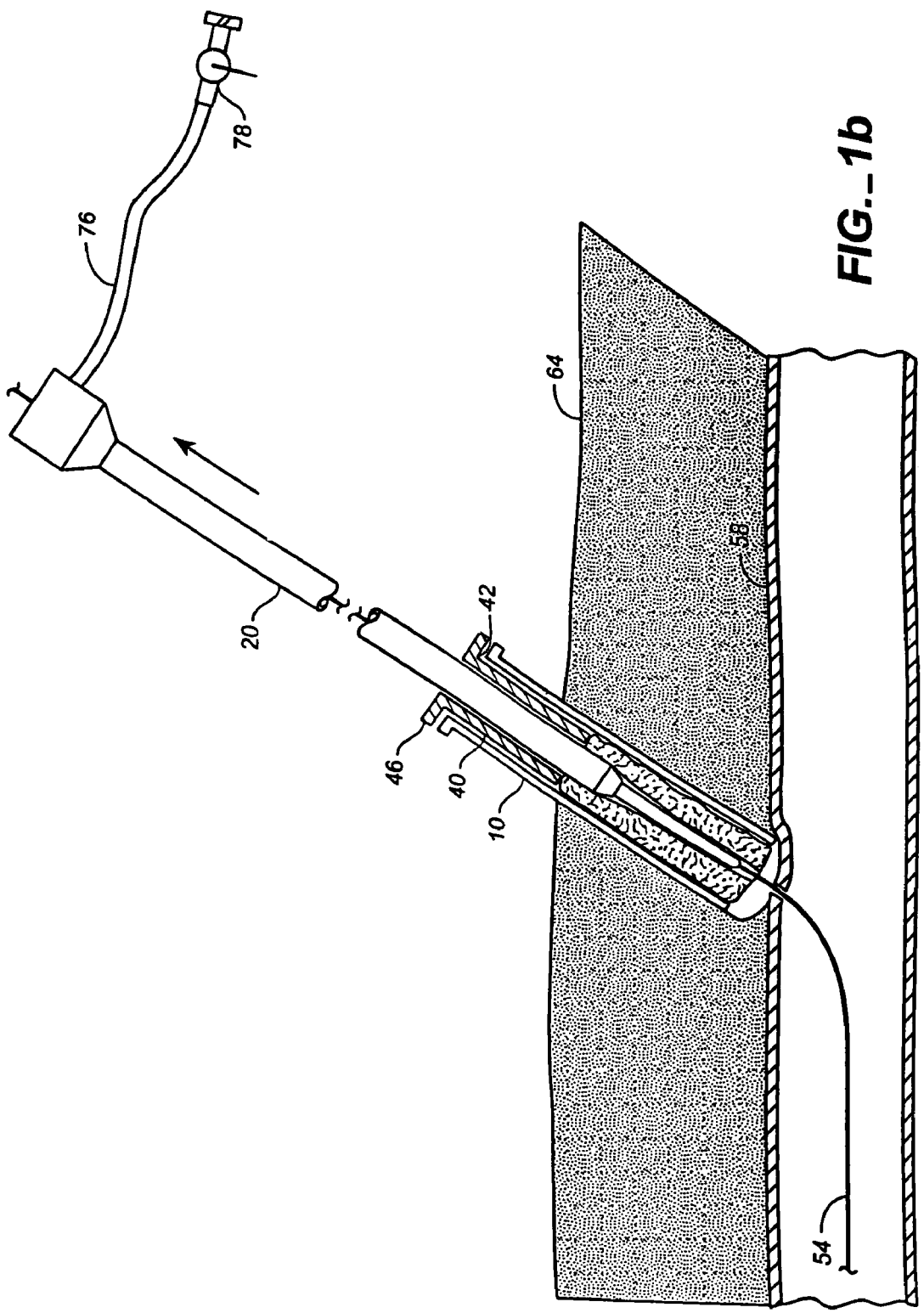
FIG._1b

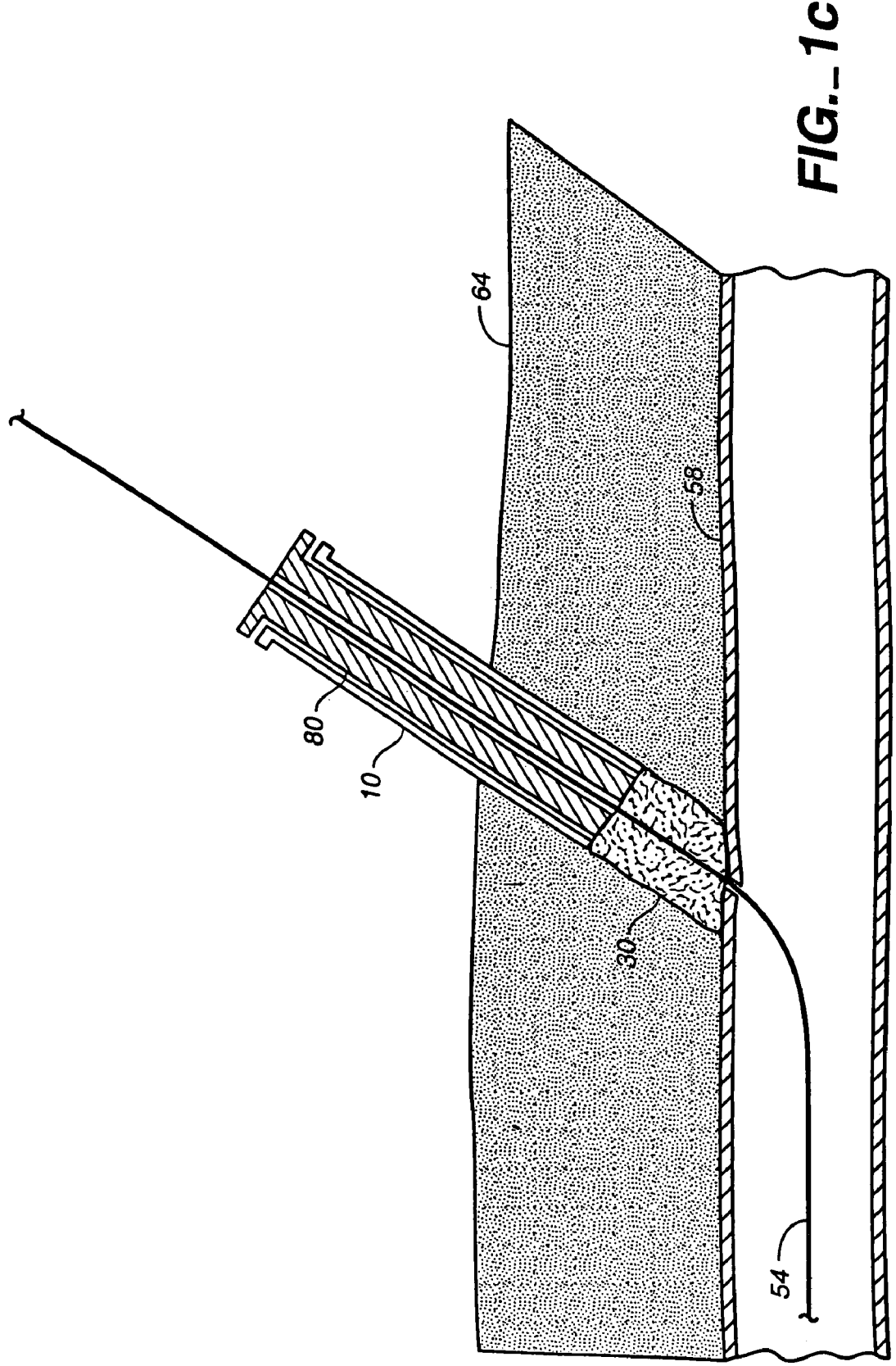

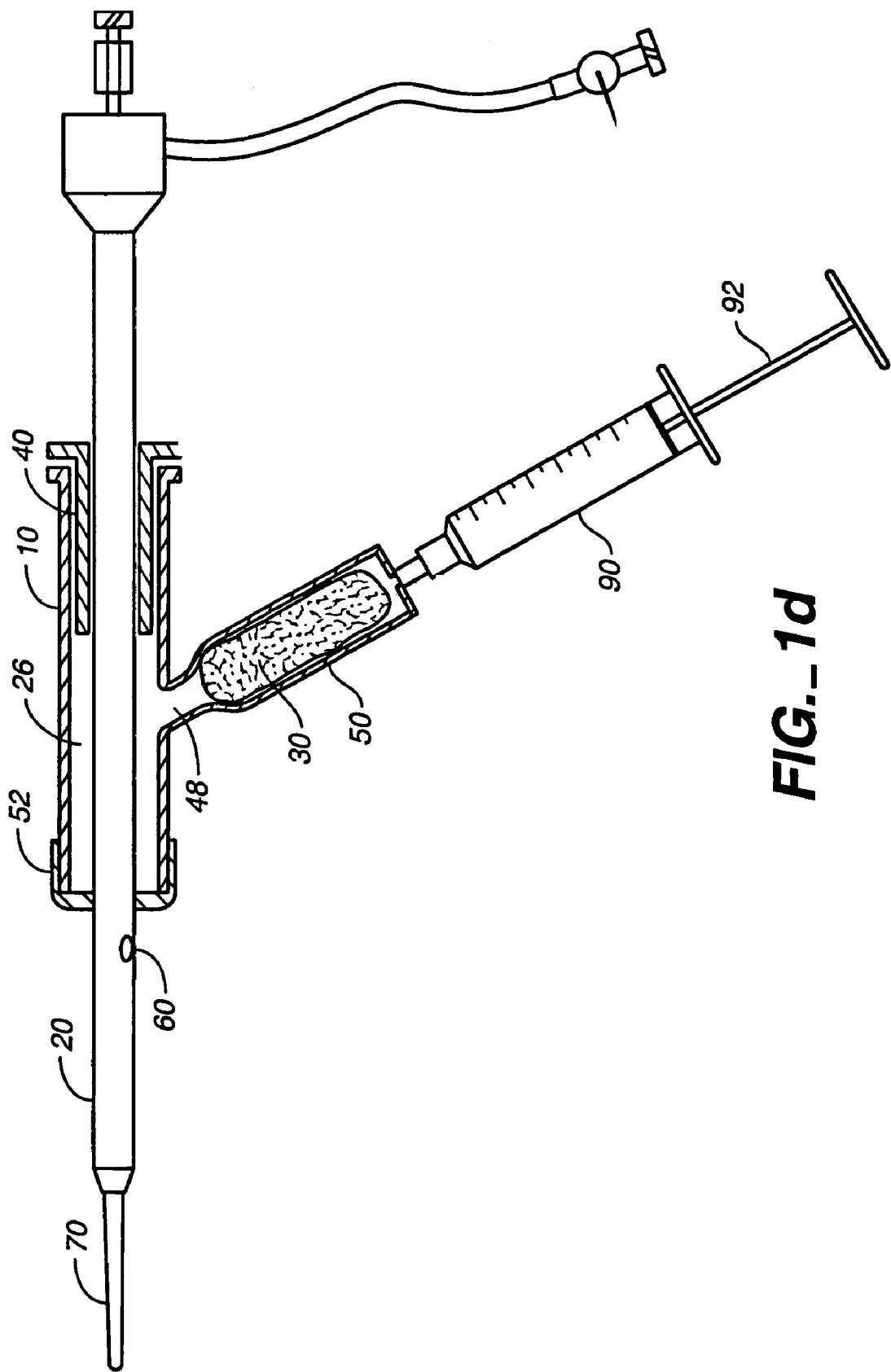
FIG._1d

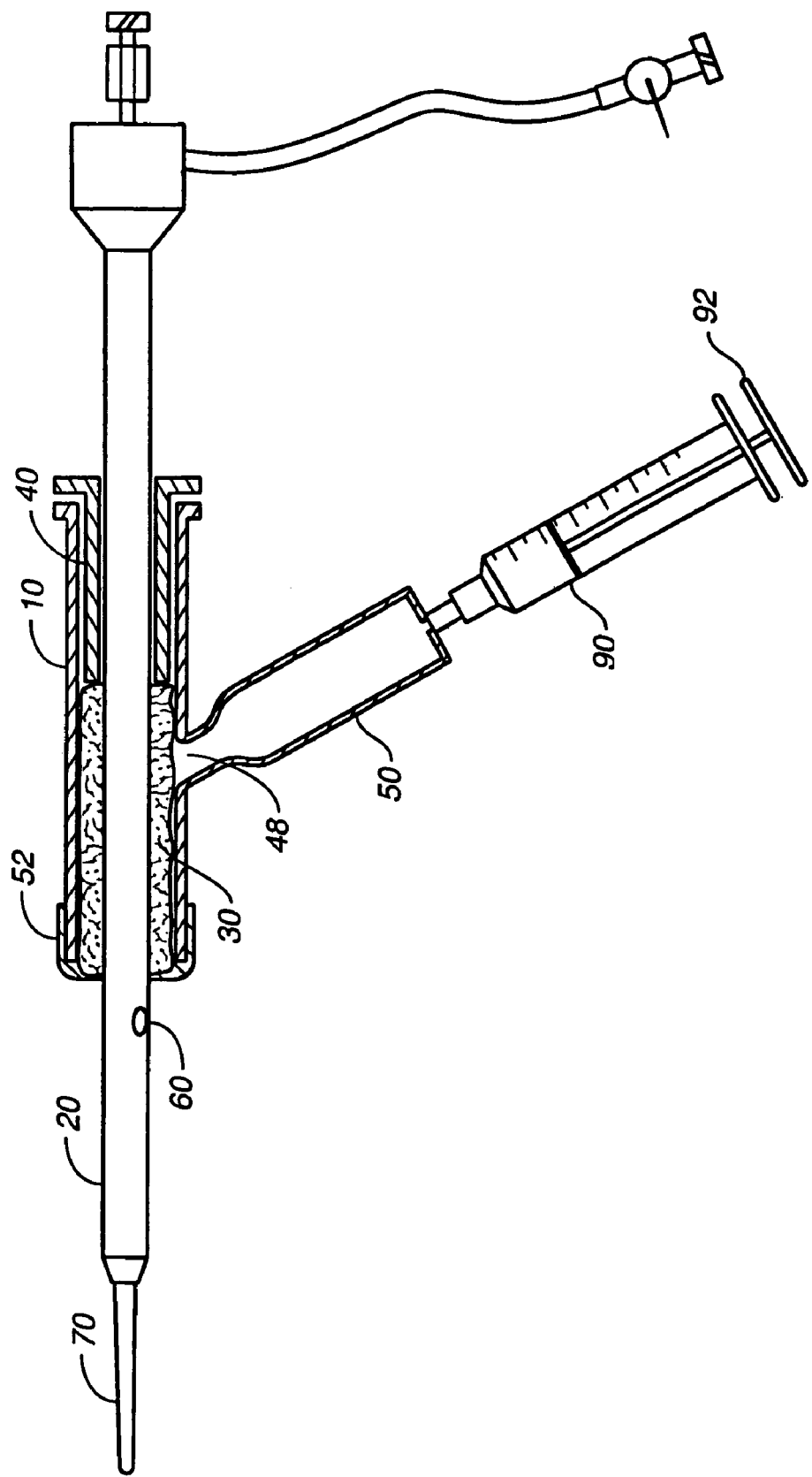
FIG._1e

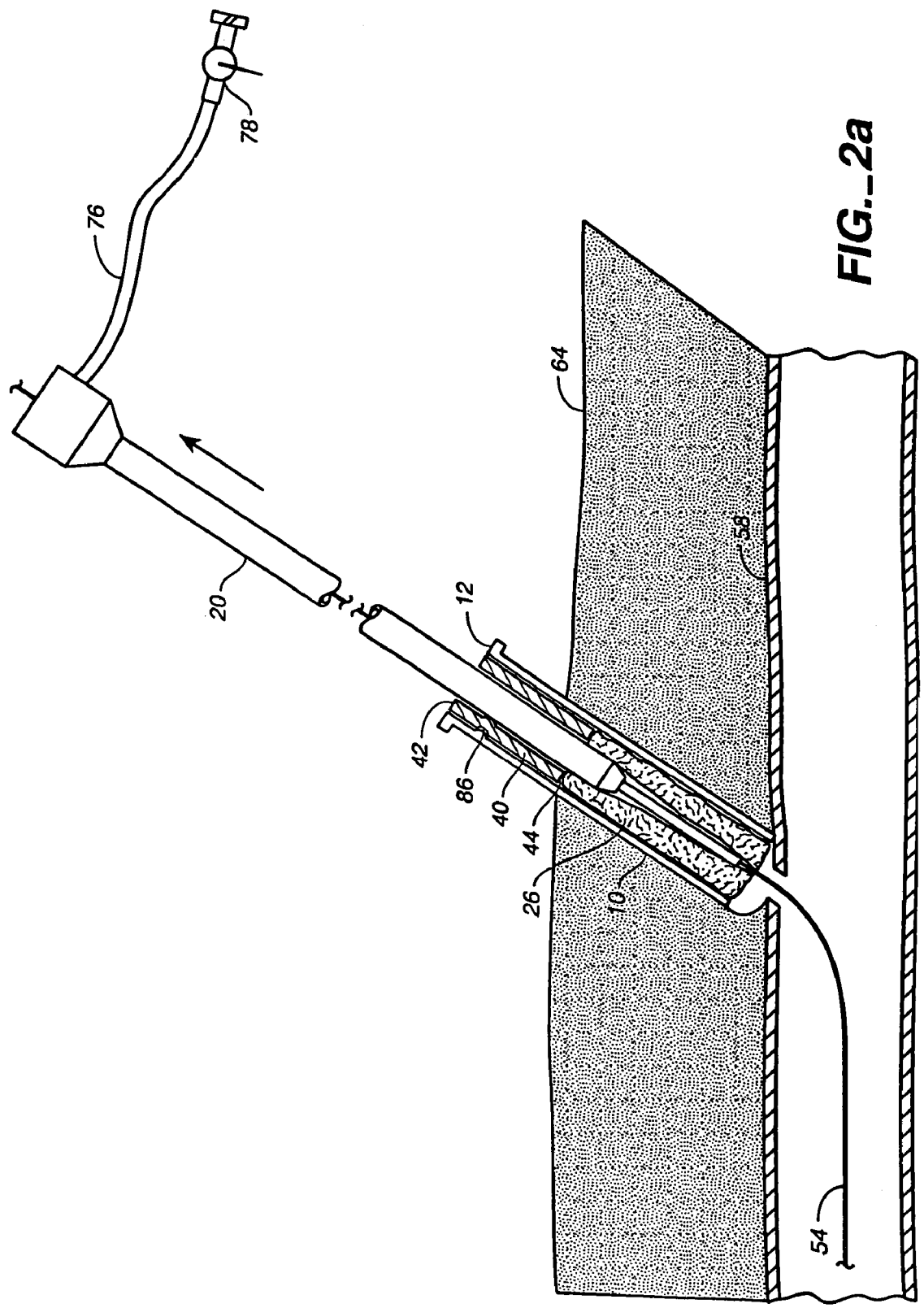
FIG._2a

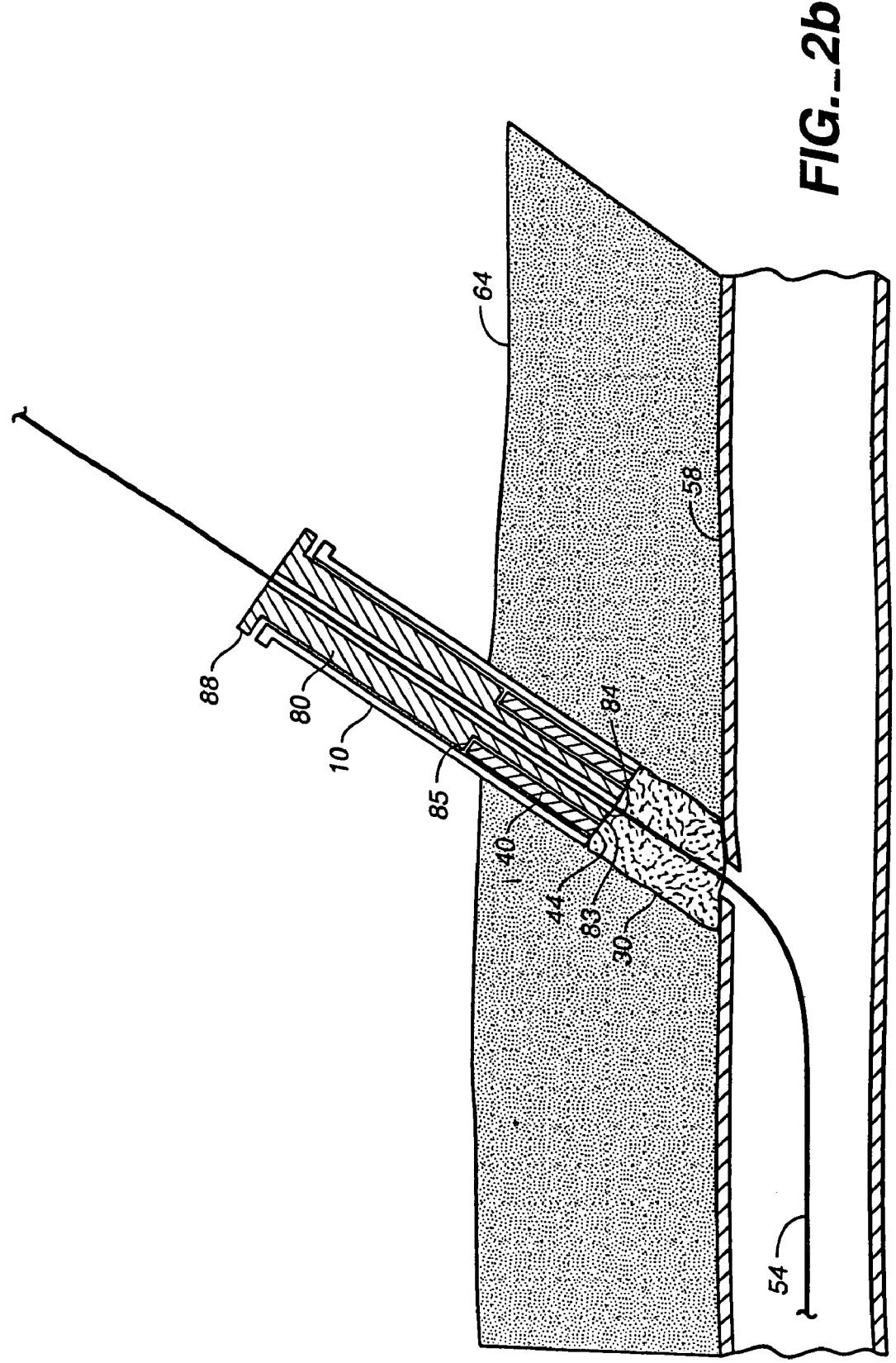
FIG._2b

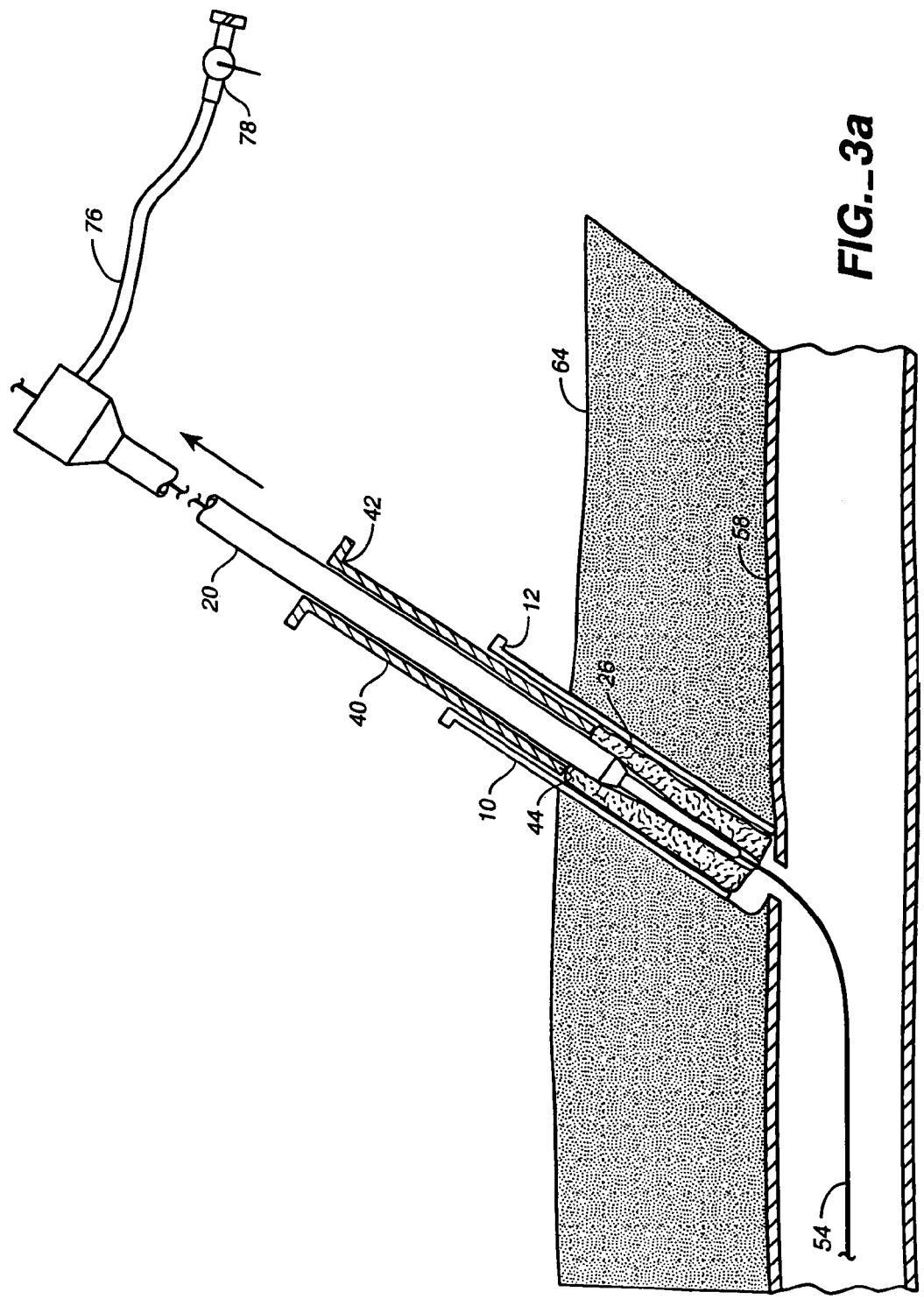

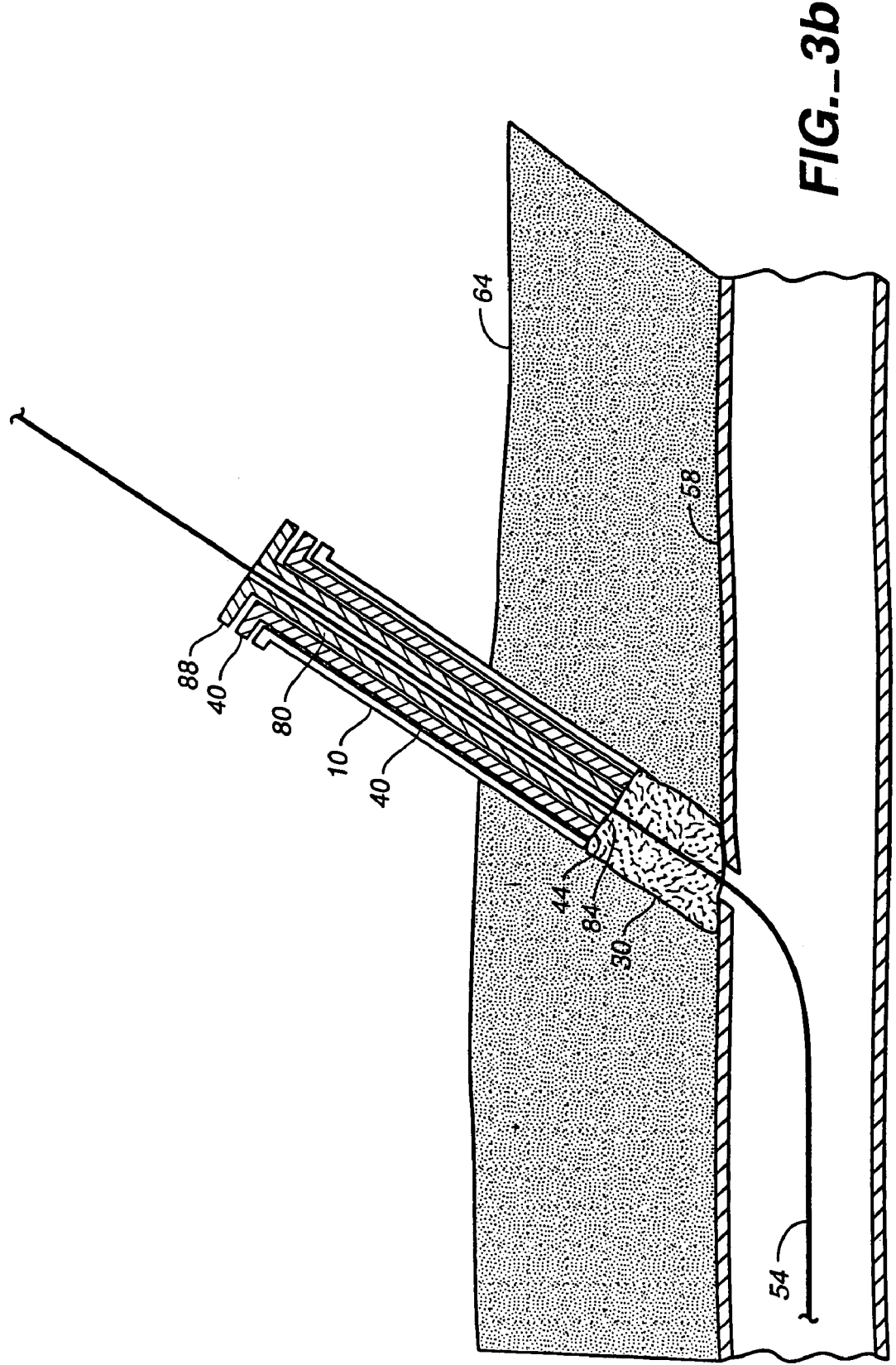
FIG._3b

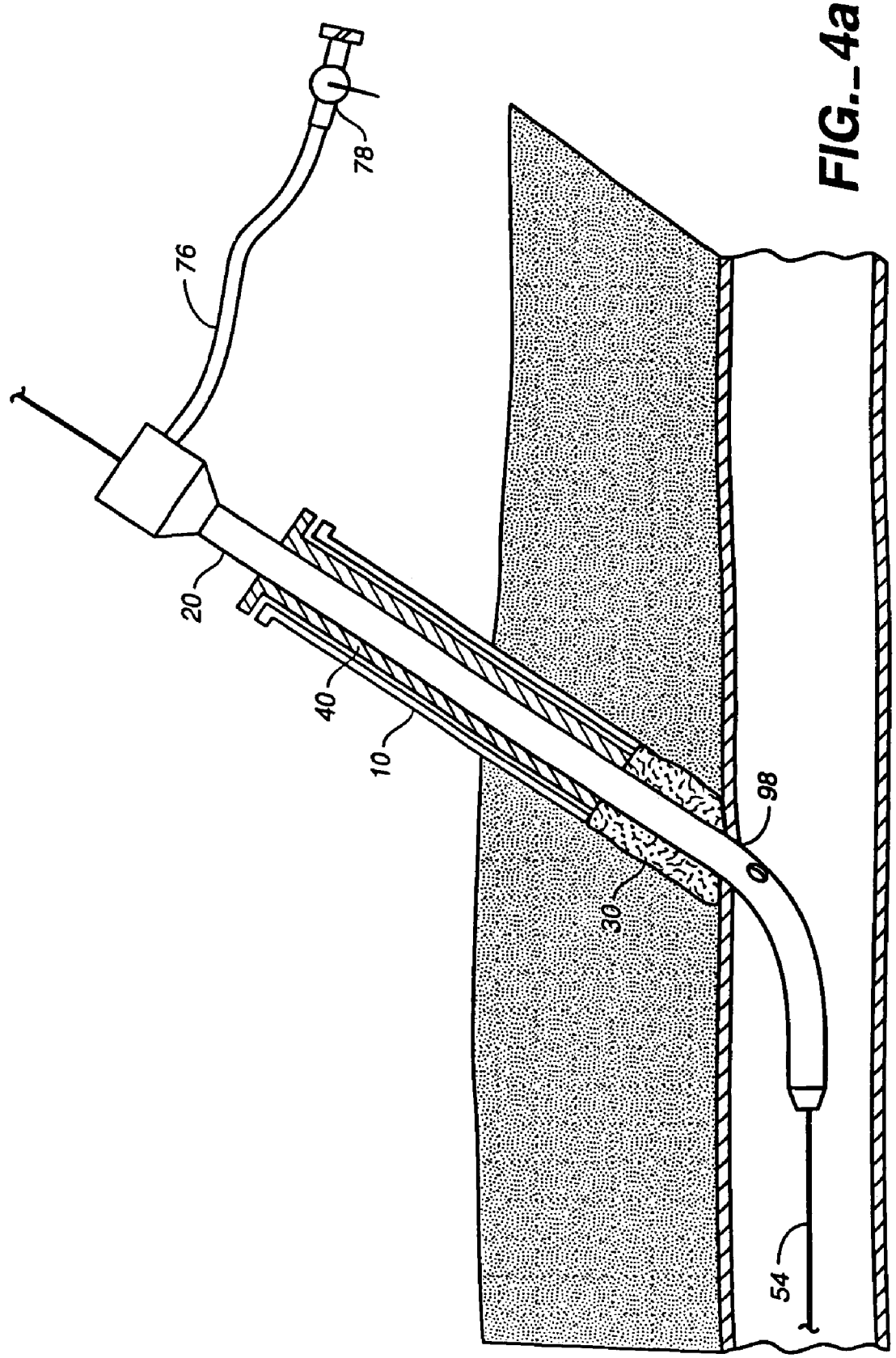

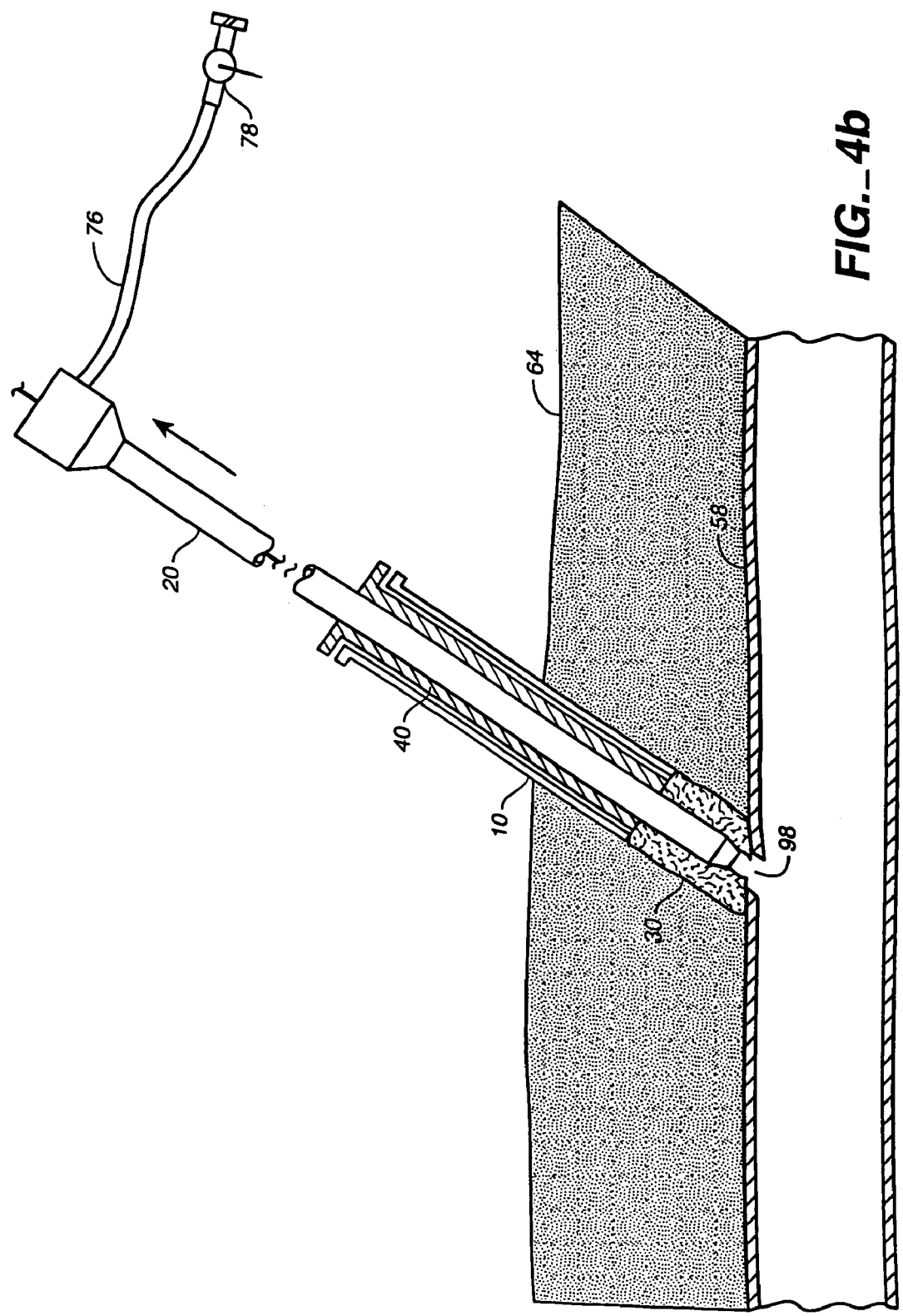
FIG._4b

SHEATH-MOUNTED ARTERIAL PLUG DELIVERY DEVICE

This application is a continuation of U.S. patent application Ser. No. 09/904,445, filed Jul. 11, 2001, now abandoned, which claims priority under 35 U.S.C. §119 to provisional U.S. patent application Ser. No. 60/218,431, filed Jul. 14, 2000. These applications are incorporated herein by reference in their entirety.

FIELD OF THE INVENTION

The present invention relates to a method and system for facilitating hemostasis of a blood vessel.

BRIEF DESCRIPTION OF THE RELATED ART

Numerous arterial puncture closure devices are known in the prior art. These include many mechanisms, such as plugs, sutures, intra-vascular structures and more. While these prior art devices vary in size and theory, they all require placement of distinct closure devices through a procedural sheath, sheath exchanges, or sheath removal prior to placement. By their very nature, these devices represent a separate procedure for access site closure after access site establishment/maintenance. The decision to use these devices is often based upon the instant availability of the device and competing demand for the doctor's time at the moment of sheath removal.

An additional challenge of puncture closure devices comes when they are deployed many hours after access has been established. In these cases, time and additional access site manipulation contribute to potential infection.

What is needed is a single device which establishes and maintains access to a puncture site, and closes the access site upon the completion of a procedure. In this way, the closure of the puncture site could become a standard of care, not subject to device availability, competing demand for doctor time, or site infection due to delayed deployment.

Accordingly, it would be desirable to provide a method and system that enable the user to access a blood vessel with a sheath that also incorporates a means for access site closure. Furthermore, upon completion of the interventional procedure, the closure device is deployed to close the puncture and the sheath is removed.

SUMMARY OF THE INVENTION

The present invention provides an improved method and system for facilitating hemostasis of a blood vessel puncture.

In accordance with one aspect of the present invention, a method of facilitating hemostasis of a blood vessel puncture includes the steps of inserting a tubular device into a puncture in a blood vessel to establish access to the blood vessel; providing a vessel closure system around the tubular device; introducing a hemostasis promoting material into a space between the tubular device and vessel closure system; and delivering the hemostatic material adjacent to the puncture to facilitate hemostasis of the puncture.

In accordance with a further aspect of the present invention, a method of facilitating hemostasis of a blood vessel puncture, the method includes inserting a procedural access sheath through a tissue tract and into a puncture in a blood vessel; providing a vessel closure system around the access sheath and at least partially in the issue tract; and performing a vascular procedure with the vessel closure system in the tissue tract.

In accordance with another aspect of the present invention, a system for facilitating hemostasis of a blood vessel puncture, the system including a delivery cannula configured to be received around an access sheath; a hemostasis promoting material within the delivery cannula for facilitating hemostasis of a blood vessel puncture when delivered adjacent to the puncture; a proximal stop for preventing proximal motion of the hemostasis promoting material within the delivery cannula when the access sheath is withdrawn proximally from the delivery cannula; and a pusher for delivering the sponge material from the delivery cannula.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1a is a perspective view of a first embodiment of a delivery cannula according to the present invention positioned for delivery of a hemostatic promoting material;

FIG. 1b is a perspective view of the delivery cannula of FIG. 1a with the access sheath being removed;

FIG. 1c is a perspective view of the delivery cannula of FIGS. 1a and 1b with the hemostatic promoting material being ejected;

FIG. 1d is a perspective view of an alternative embodiment of a delivery cannula with a side staging chamber;

FIG. 1e is a perspective view of the delivery cannula of FIG. 1d with the hemostatic promoting material in the delivery cannula;

FIG. 2a is a perspective view of a delivery cannula according to an alternative embodiment;

FIG. 2b is a perspective view of a delivery cannula according to an alternative embodiment;

FIG. 3a is a perspective view of a delivery cannula according to an alternative embodiment;

FIG. 3b is a perspective view of a delivery cannula according to another embodiment;

FIG. 4a is a perspective view of a delivery cannula according to another embodiment; and FIG. 4b is a perspective view of a delivery cannula according to an alternative embodiment.

DETAILED DESCRIPTION OF THE PREFERRED EMBODIMENTS

The present invention provides an access system that enables the user to access a blood vessel with a sheath that also incorporates a means for performing site closure. Upon completion of the interventional procedure, the closure device is deployed to close the puncture and the sheath is removed.

As shown in FIG. 1a, an access system for facilitating hemostasis of a blood vessel includes a delivery cannula 10 positioned coaxially around an access sheath 20, and a hemostatic promoting material 30 within the delivery cannula 10 for facilitating hemostasis of a blood vessel puncture when delivered adjacent to the puncture. In one preferred embodiment, the hemostatic material 30 is a hydrated and compressed sponge.

The delivery cannula 10 as shown in FIG. 1a is dimensioned such that its proximal end 12 can attach to the access sheath 20 at or near the access sheath proximal end 22, and such that the delivery cannula 10 distal end 14 terminates proximal to the distal end 24 of the access sheath 20. Further, the delivery cannula 10 incorporates an annular proximal stop 40 fitting slideably around the access sheath 20 and removably within the delivery cannula 10. The proximal stop 40 is positioned within the delivery cannula 10 such that its distal end 44 defines the proximal boundary of a coaxial hemostatic material space 26. The proximal end 42 of the proximal stop 40 is positioned at or near the proximal end 12 of the delivery cannula 10. The proximal stop 40 may include a proximal flange 46 to facilitate proper placement within the delivery cannula 10.

While the hemostatic material space 26 described herein is coaxial, it can be appreciated that many other configurations are possible. The hemostatic material space 26 is defined by the outside of the access sheath 20 and the inside of the delivery cannula 10 and may be continuous, discontinuous, symmetrical, or nonsymmetrical.

In one preferred embodiment as shown in FIG. 1a, the access system is prepared by attaching the delivery cannula 10 to the access sheath 20 as described above. The hemostatic material 30 is then introduced into the coaxial space 26 between the delivery cannula 10 and access sheath 20.

In another preferred embodiment, as shown in FIGS. 1d & 1e the hemostatic material 30 is introduced into the coaxial space 26 by hydrating an absorbable sponge in a staging chamber portion 50 of the delivery cannula 10 and advancing the sponge through a side port 48 of the delivery cannula into a delivery position surrounding the access sheath 20. The hydrating of the absorbable sponge is performed with a syringe 90 and a syringe plunger 92. A removable distal stop or vent 52 may be provided to help position the hemostatic material 30 within the system. Alternatively, the distal stop or vent 52 may be soluble and/or absorbable such that it remains in place during advancement of the system into the vascular access site and then dissolves to allow delivery of the hemostatic material. A distal stop or vent 52 of this type may be made of gelatin, polyglycolic acid, or other suitable material known to one skilled in the art.

The system can then be placed much like an ordinary access sheath 20 as shown in FIG. 1a. The removable distal stop or vent 52 is removed (if present) and the system is placed over a guidewire 54 and into the vascular access site such that the portion of the access sheath 20 extending distally beyond the distal end of the delivery cannula 10 extends through a vessel puncture 55 and into a vessel 57 and the distal end of the delivery cannula 10 resides at or near the outer blood vessel wall 58. A bleed-back hole 60 in the access sheath 20 can be utilized to provide bleed-back as an indication that the distal end 14 of the delivery cannula 10 is within a predetermined proximity with respect to the blood vessel 58. The lack of bleed-back 62 indicates a more proximal location of the delivery cannula 10. The delivery cannula 10 may be positioned using only bleed-back 62 as an indicator of position, or may be more precisely located by utilizing tactile feedback as the enlarged distal end of the delivery cannula 10 encounters the outer blood vessel wall 58.

Bleed-back 62 is facilitated by providing a dilator 70 within the access sheath 20 that fits closely over the guidewire 54 at its distal end 74 such that it substantially prevents blood from entering the dilator 70. Further, the dilator 70 fits closely within the distal access sheath 20 such that it substantially prevents blood from entering the access sheath. In this way, blood is restricted from entering the access sheath 20 until the bleed-back hole 60 enters the blood vessel 58. Blood entering the bleed-back hole 60 might then exit the patient through a number of paths.

If the access sheath 20 was provided with a seal at its proximal end 22, the blood might enter a hole in the dilator 70 and then exit the proximal end 72 of the dilator 70. Alternatively, blood could flow between the dilator 70 and access sheath 20 to an exit in the introduction port 76 and stop-cock 78 as shown in FIG. 1a. If the access sheath 20 has no proximal seal, the blood could exit the proximal end 22 of the access sheath 20.

In operation, the access systems of the present invention are used as follows. The interventional procedure is conducted as usual with the delivery cannula 10 and hemostatic material 30 in place during the procedure. At the end of the interventional procedure, the access sheath 20 portion of the system is detached from the delivery cannula 10 and fully withdrawn while the delivery cannula 10 and proximal stop 40 remain stationary as shown in FIG. 1b. The proximal stop 40 prevents the hemostatic material 30 from moving proximally during access sheath 20 removal. This portion of the procedure may take place with or without a guidewire 54 in place.

The proximal stop 40 is then removed from the delivery cannula 10 and a pusher 80 having an outside diameter just smaller than the inside diameter of the delivery cannula 10 is placed over the guidewire 54 (if present) and advanced until it contacts the proximal portion of hemostatic material 30. As shown in FIG. 1c, the hemostatic material 30 is then delivered by moving the delivery cannula 10 proximally with respect to the pusher 80.

In one preferred embodiment, the pusher 80 is held stationary while the delivery cannula 10 is withdrawn. It is also understood that the pusher 80 can be advanced while the delivery cannula 10 is held stationary. It is further understood that any combination of these techniques can result in delivery of hemostatic material 30. After delivering hemostatic material 30 into the desired site, the guidewire 54 (if present) and the pusher 80 and cannula 10 are removed from the puncture tract.

In an alternative embodiment, as shown in FIG. 2a, a proximal stop 40 is positioned within the delivery cannula 10 such that its distal end 44 defines the proximal boundary of the coaxial hemostatic material space 26. The proximal end 42 of the proximal stop 40 terminates at the proximal end 12 of the delivery cannula 10. Detent 86 features such as bumps or ratchets may be included on the inside of the delivery cannula 10 or the outside of the proximal stop 40 to releasibly hold the proximal stop 40 in place. Upon completion of the interventional procedure, the access sheath 20 portion of the system is withdrawn while the delivery cannula 10 and proximal stop 40 remain stationary as shown in FIG. 2a. The proximal stop 40 prevents the hemostatic material 30 from moving proximally during access sheath 20 removal. This portion of the procedure may take place with or without a guidewire 54 in place.

A pusher 80 shown in FIG. 2b, having a distal portion 83 with an outside diameter similar to the previously removed access sheath 20 and a length similar to the proximal stop 40 is then placed over the guidewire 54 (if present) and advanced into the proximal stop 40 until its distal end 84 is approximately aligned with the distal end 44 of the proximal stop 40. The pusher 80 may be provided with a proximal shoulder 85 to facilitate this alignment. As shown in FIG. 2b, the hemostatic material 30 is then delivered by moving the delivery cannula 10 proximally with respect to the pusher 80 and proximal stop 40. In one preferred embodiment, the pusher 80 and proximal stop 40 are held stationary while the delivery cannula 10 is withdrawn. The pusher 80 may include a proximal flange 88 to beneficially limit its movement with respect to the delivery cannula 10. After delivering hemostatic material 30 into a desired site, the guidewire 54 (if present) and system are removed.

In an alternative embodiment, as shown in FIG. 3a, a longer proximal stop 40 is positioned within the delivery cannula 10 such that its distal end 44 defines the proximal boundary of the coaxial hemostatic material space 26. The proximal end 42 of the proximal stop 40 extends beyond the proximal end 12 of the delivery cannula 10 a distance equal to or greater than the length of the coaxial hemostatic material space 26. Upon completion of the interventional procedure, the access sheath 20 portion of the system is detached from the delivery cannula 10 and fully withdrawn while the delivery cannula 10 and proximal stop 40 remain stationary. The proximal stop 40 is held in place manually or with a locking mechanism to prevent the hemostatic material 30 from moving proximally during access sheath 20 removal. This portion of the procedure may take place with or without a guidewire 54 in place.

As shown in FIG. 3b, a pusher 80 having an outside diameter similar to the previously removed access sheath 20 and a length similar to the proximal stop 40 is then placed over the guidewire 54 (if present) and advanced into the proximal stop 40 until its distal end 84 is approximately aligned with the distal end 44 of the proximal stop 40. The pusher 80 may be provided with a proximal flange to facilitate this alignment. The hemostatic material 30 is then delivered by moving the delivery cannula 10 proximally with respect to the pusher 80 and proximal stop 40 as shown in FIG. 3b. In one preferred embodiment, the pusher 80 and proximal stop 40 are held stationary while the delivery cannula 10 is withdrawn. The proximal stop 40 may include a proximal flange to beneficially limit its movement with respect to the delivery cannula. After delivering hemostatic material 30 into desired site, the guidewire 54 (if present) and system are removed.

In still another embodiment shown in FIG. 4a, a proximal stop 40 similar to that just described is used to deliver the hemostatic material without the use of a pusher 80. A system incorporating this type of proximal stop 40 is placed within an access site. At the end of the interventional procedure and prior to access sheath 20 removal, the delivery cannula 10 is moved proximally with respect to the proximal stop 40 as shown in FIG. 4a. In this way the hemostatic material 30 is delivered to the desired site with the access sheath 20 still in place. The access sheath 20 provides hemostasis at the puncture site 98 during hemostatic material 30 delivery and also prevents hemostatic material 30 from entering the puncture site 98.

As shown in FIG. 4b, the delivery cannula 10 and proximal stop 40 are then held stationary to stabilize the hemostatic material 30 while the access sheath 20 is removed. The delivery cannula 10 and proximal stop 40 can then be removed from the site. Note that the guidewire 54 (if present) can be removed before the access sheath 20 is removed, when the access sheath 20 is removed, after the access sheath 20 is removed, or after the delivery cannula 10 and proximal stop 40 are removed.

Other means of positioning the hemostatic material within the system include placing the hemostatic material within the distal lumen of the delivery cannula 10 and then passing the access sheath 20 through it.

In another preferred embodiment the hemostatic promoting material 30 is placed in the cannula by placing a hydrated sponge within the distal end 14 of the delivery cannula 10. The distal end 24 of the access sheath 20 with a stylet or obturator placed within it is then advanced into the proximal end 12 of the delivery cannula 10 and through the sponge until the distal access sheath 20 protrudes beyond the distal end 14 of the delivery cannula 10. The stylet or obturator is then removed to ready the system for placement into an access site.

The absorbable sponge material can be absorbed by the body in a period of time between several days and several months depending on the absorbable sponge material used. A pledget formed of commercially available Gelfoam material will be absorbed by the body within 1 to 6 weeks. However, the pledget material may be engineered to provide different rates of absorption. For example, Gelfoam can be designed to be absorbed at different rates by varying the degree of crosslinking. Preferably, the pledget is designed to be absorbed in less than one month.

Although the invention is primarily intended for delivery of absorbable sponge, non-absorbable sponge may also be delivered with the devices, systems, and methods of the present invention. A non-absorbable sponge may be desirable where it will be necessary to locate the blood vessel puncture after the procedure.

While an amorphous or discontinuous sponge structure may be used in the present invention, a continuous structure of the delivered absorbable sponge pledget provides more secure and reliable placement of a plug of material against the blood vessel puncture than a paste or liquid. The continuous sponge structure can even facilitate partial withdrawal, removal, or movement of the ejected pledget.

The absorbable sponge material can be hydrated with a clotting agent such as thrombin, a contrast agent, another beneficial agent, a combination of agents, or the like. Alternatively, the pledget material itself may contain an agent such as a clotting agent, a contrast agent, another beneficial agent, a combination of agents, or the like.

The absorbable sponge pledget may be presoaked with a beneficial agent such as thrombin for delivery of the beneficial agent to the punctured blood vessel. Alternatively, the pledget may be hydrated with a beneficial liquid agent used as the hydrating fluid within a syringe. Further, the beneficial agent may be delivered to the pledget after the pledget is ejected at the blood vessel puncture site through the lumen of the pusher 80, through the delivery cannula 10, through the access sheath 20 or through the dilator 70.

Because the amount of subcutaneous fat and tissue between the skin 64 and the blood vessel wall 58 varies between patients from approximately 0.5 cm to 15 cm or more the system may be provided in different lengths for use in different patients. The pledget size and shape may also be varied for different patients. The absorbable sponge material should form a complete plug over the puncture site without expanding into the blood vessel or exiting the skin of the patient. In some instances where the amount of subcutaneous tissue is great it may be desirable to deliver multiple pledgets in spaced apart positions along the tract leading to the puncture site.

The particular size and shape of the access system may vary depending on the size of the access site, amount of subcutaneous tissue, and the size of pledget to be delivered. According to one example of the present invention, a pledget is formed from a rectangular piece of pre-compressed Gelfoam approximately 2 by 3 cm with a thickness of 0.15 cm. The Gelfoam is rolled or folded into a pledget having a length of approximately 3 cm. An introducer for delivery of this pledget to a patient with an average amount of subcutaneous tissue has a staging chamber length of about 2.5 to 6 cm, preferably approximately 3 cm, a staging chamber inner diameter of about 0.12 to 1.5 cm, preferably about 0.3 cm to about 0.6 cm, and a delivery chamber which is typically longer than the staging chamber and has an inner diameter smaller than that of the staging chamber of about 1 cm or less, preferably approximately 0.33 cm or less. The particular length of the delivery chamber depends on both the subcutaneous tissue depth of the patient and the linear expansion of the pledget as it moves from the staging chamber to the delivery chamber. An angle made by a wall of the tapered section 38 with a longitudinal axis of the adaptor may vary from about 5° to 90°, but is preferably between about 30° and 60°, more preferably approximately 45°. The tapered section 38 is illustrated with a substantially planar interior surface, when shown in cross section. However, the tapered section may also have a convex or concave surface in cross-section. This example of pledget and introducer configurations is merely exemplary of the present invention.

In addition, the hemostatic promoting material 30 may be inserted into the cannula in a dry form and hydrated in the cannula. Alternatively, the hemostatic material may be hydrated prior to staging in the cannula, hydrated after delivery or any combination thereof.

While the invention has been described in detail with reference to the preferred embodiments thereof, it will be apparent to one skilled in the art that various changes and modifications can be made and equivalents employed, without departing from the present invention.

The invention claimed is:

1. A method of facilitating hemostasis of a blood vessel puncture, the method comprising:
    inserting a tubular device into a puncture in a blood vessel to establish access to the blood vessel;
    providing a vessel closure system around the tubular device;
    providing a proximal stop having a distal end adapted to be disposed within a space between the vessel closure system and the tubular device, the proximal stop defining a single chamber aperture sized to receive the tubular device;
    introducing a hemostasis promoting material into the space between the tubular device and vessel closure system, the hemostasis promoting material being situated distal to a distal end of the proximal stop;
    withdrawing the tubular device completely from the vessel closure system;
    inserting a pusher into the vessel closure system after the tubular device is withdrawn, the pusher being separate from the proximal stop and including a distal end sized for insertion into the single chamber aperture of the proximal stop; and
    effecting proximal movement of the vessel closure system with respect to the pusher to deliver the hemostasis material adjacent to the puncture and facilitate hemostasis of the puncture.

2. The method of claim 1, further comprising a step of locating the puncture by using a bleed-back hole in the tubular device.

3. The method of claim 1, further comprising a step of locating the puncture by using tactile feedback.

4. The method of claim 1, further comprising a step of hydrating the hemostatic material with a syringe.

5. The method of claim 1, further comprising a step of positioning the hemostatic material within the system using a distal stop or vent.

6. The method of claim 1, further comprising a step of placing the tubular device and vessel closure system over a guidewire.

7. The method of claim 6, further comprising a step of removing the guidewire after the hemostatic material is delivered.

8. The method of claim 1, further comprising a step of facilitating bleed-back by providing a dilator within the tubular device.

9. The method of claim 1, further comprising a step of removing the proximal stop from the vessel closure system.

10. The method of claim 1, further comprising a step of holding the pusher stationary while the vessel closure system is withdrawn.

11. The method of claim 1, further comprising a step of advancing the pusher while the vessel closure system is held stationary.

12. The method of claim 1, further comprising a step of removing the vessel closure system after the hemostatic material is delivered.

13. The method of claim 1, further comprising a step of removing the tubular device while the vessel closure system and proximal stop remain stationary.

14. The method of claim 1, further comprising a step of withdrawing the vessel closure system while holding the pusher and proximal stop stationary.

15. The method of claim 1, further comprising a step of withdrawing the vessel closure system by moving the vessel closure system proximal with respect to the proximal stop.

16. The method of claim 1, further comprising a step of placing a hydrated sponge within the vessel closure system and withdrawing the tubular device prior to delivery of the hydrated sponge.

17. The method of claim 1, further comprising a step of advancing a stylet or obturator into the tubular device.

* * * * *

UNITED STATES PATENT AND TRADEMARK OFFICE
CERTIFICATE OF CORRECTION

PATENT NO. : 7,621,936 B2
APPLICATION NO. : 10/754824
DATED : November 24, 2009
INVENTOR(S) : Cragg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 651 days.

Signed and Sealed this

Twenty-sixth Day of October, 2010

David J. Kappos
*Director of the United States Patent and Trademark Office*